(12) United States Patent
Gustavson et al.

(10) Patent No.: US 11,896,829 B2
(45) Date of Patent: *Feb. 13, 2024

(54) NETWORK-ACCESSIBLE DATA ABOUT PATIENT WITH WEARABLE CARDIAC DEFIBRILLATOR SYSTEM

(71) Applicant: WEST AFFUM HOLDINGS DAC, Dublin (IE)

(72) Inventors: Laura Marie Gustavson, Redmond, WA (US); David Peter Finch, Bothell, WA (US); Erick Michael Roane, Kirkland, WA (US); Jason Fouts, Bothell, WA (US)

(73) Assignee: West Affum Holdings DAC, Dublin (IE)

( * ) Notice: Subject to any disclaimer, the term of this patent is extended or adjusted under 35 U.S.C. 154(b) by 40 days.

This patent is subject to a terminal disclaimer.

(21) Appl. No.: 17/590,620

(22) Filed: Feb. 1, 2022

(65) Prior Publication Data

US 2022/0152403 A1 May 19, 2022

Related U.S. Application Data

(63) Continuation of application No. 16/593,898, filed on Oct. 4, 2019, now Pat. No. 11,247,058, which is a (Continued)

(51) Int. Cl.
*A61N 1/39* (2006.01)
*A61N 1/372* (2006.01)
(Continued)

(52) U.S. Cl.
CPC ........ *A61N 1/37211* (2013.01); *A61N 1/3937* (2013.01); *A61N 1/3993* (2013.01);
(Continued)

(58) Field of Classification Search
CPC .......... A61N 1/37211; A61N 1/3937; A61N 1/3993; G16H 10/60; G16H 20/30;
(Continued)

(56) References Cited

U.S. PATENT DOCUMENTS 3,724,355 A 4/1973 Busch et al.
4,583,524 A 4/1986 Hutchins
(Continued)

FOREIGN PATENT DOCUMENTS

DE 2005060985 A2 6/2007
EP 2305110 A1 4/2011
(Continued)

OTHER PUBLICATIONS

Heartstart MRx and XL AED Algorithm—Application Note, Jul. 2001, Edition 2 Philips Healthcare, USA.
(Continued)

*Primary Examiner* — Maroun P Kanaan
(74) *Attorney, Agent, or Firm* — Christensen O'Connor Johnson Kindness PLLC

(57) ABSTRACT

A data file system includes one or more files about a patient wearing a wearable cardiac defibrillator (WCD) system that has been assigned to them. The one or more files contain at least one patient identifier of the patient, compliance data about a history of the patient's wearing the WCD system, and possibly other data. The data file system can be accessed through a communication network when the patient uses a communication device. When so accessed, some of the contents can be viewed on a screen of the device, for example in the form of a website. In embodiments, the health care provider and friends and family can view such data and even enter inputs, which may create a situation that motivates the patient to comply better.

20 Claims, 11 Drawing Sheets

Related U.S. Application Data continuation of application No. 14/580,183, filed on Dec. 22, 2014, now Pat. No. 10,449,370.

(60) Provisional application No. 61/992,850, filed on May 13, 2014.

(51) Int. Cl.

| | | |
|---|---|---|
| *G16H 10/60* | (2018.01) | |
| *G16H 40/63* | (2018.01) | |
| *G16H 20/40* | (2018.01) | |
| *G16H 20/30* | (2018.01) | |
| *G16H 40/67* | (2018.01) | |
| *G16H 15/00* | (2018.01) | |

(52) U.S. Cl.
CPC ............ *G16H 10/60* (2018.01); *G16H 20/30* (2018.01); *G16H 20/40* (2018.01); *G16H 40/63* (2018.01); *G16H 40/67* (2018.01); *G16H 15/00* (2018.01)

(58) Field of Classification Search
CPC ........ G16H 20/40; G16H 40/63; G16H 40/67; G16H 15/00
See application file for complete search history.

(56) References Cited

U.S. PATENT DOCUMENTS

| | | | |
|---|---|---|---|
| 4,619,265 | A | 10/1986 | Morgan et al. |
| 4,666,432 | A | 5/1987 | McNeish et al. |
| 4,698,848 | A | 10/1987 | Buckley |
| 4,928,690 | A | 5/1990 | Heilman et al. |
| 4,955,381 | A | 9/1990 | Way et al. |
| 5,078,134 | A | 1/1992 | Heilman et al. |
| 5,228,449 | A | 7/1993 | Christ et al. |
| 5,348,008 | A | 9/1994 | Bornn et al. |
| 5,353,793 | A | 10/1994 | Bornn |
| RE34,800 | E | 11/1994 | Hutchins |
| 5,394,892 | A | 3/1995 | Kenny et al. |
| 5,405,362 | A | 4/1995 | Kramer et al. |
| 5,429,593 | A | 7/1995 | Matory |
| 5,474,574 | A | 12/1995 | Payne et al. |
| 5,618,208 | A | 4/1997 | Crouse et al. |
| 5,662,690 | A | 9/1997 | Cole et al. |
| 5,708,978 | A | 1/1998 | Johnsrud |
| 5,741,306 | A | 4/1998 | Glegyak et al. |
| 5,782,878 | A | 7/1998 | Morgan et al. |
| 5,792,204 | A | 8/1998 | Snell |
| 5,902,249 | A | 5/1999 | Lyster |
| 5,913,685 | A | 6/1999 | Hutchins |
| 5,944,669 | A | 8/1999 | Kaib |
| 6,047,203 | A | 4/2000 | Sackner et al. |
| 6,065,154 | A | 5/2000 | Hulings et al. |
| 6,108,197 | A | 8/2000 | Janik |
| 6,148,233 | A | 11/2000 | Owen et al. |
| 6,201,992 | B1 | 3/2001 | Freeman |
| 6,263,238 | B1 | 7/2001 | Brewer et al. |
| 6,280,461 | B1 | 8/2001 | Glegyak et al. |
| 6,287,328 | B1 | 9/2001 | Snyder et al. |
| 6,304,780 | B1 | 10/2001 | Owen et al. |
| 6,319,011 | B1 | 11/2001 | Motti et al. |
| 6,334,070 | B1 | 12/2001 | Nova et al. |
| 6,356,785 | B1 | 3/2002 | Snyder et al. |
| 6,427,083 | B1 | 7/2002 | Owen et al. |
| 6,437,083 | B1 | 8/2002 | Brack et al. |
| 6,450,942 | B1 | 9/2002 | Lapanashvili et al. |
| 6,529,875 | B1 | 3/2003 | Nakajima et al. |
| 6,546,285 | B1 | 4/2003 | Owen et al. |
| 6,671,545 | B2 | 12/2003 | Fincke |
| 6,681,003 | B2 | 1/2004 | Linder et al. |
| 6,762,917 | B1 | 7/2004 | Verbiest et al. |
| 7,065,401 | B2 | 6/2006 | Worden |
| 7,559,902 | B2 | 7/2009 | Ting et al. |
| 7,753,759 | B2 | 7/2010 | Pintor et al. |
| 7,865,238 | B2 | 1/2011 | Brink |
| 7,870,761 | B2 | 1/2011 | Valentine et al. |
| 7,974,689 | B2 | 7/2011 | Volpe et al. |
| 8,135,462 | B2 | 3/2012 | Owen et al. |
| 8,140,154 | B2 | 3/2012 | Donnelly et al. |
| 8,369,944 | B2 | 2/2013 | Macho et al. |
| 8,527,028 | B2 | 9/2013 | Kurzweil et al. |
| 8,548,557 | B2 | 10/2013 | Garstka et al. |
| 8,560,044 | B2 | 10/2013 | Kurzweil et al. |
| 8,615,295 | B2 | 12/2013 | Savage et al. |
| 8,644,925 | B2 | 2/2014 | Volpe et al. |
| 8,676,313 | B2 | 3/2014 | Volpe et al. |
| 8,706,255 | B2 | 4/2014 | Phillips et al. |
| 8,742,349 | B2 | 6/2014 | Urbon et al. |
| 8,838,235 | B2 | 9/2014 | Cowan et al. |
| 8,897,860 | B2 | 11/2014 | Volpe et al. |
| 8,904,214 | B2 | 12/2014 | Volpe et al. |
| 8,965,500 | B2 | 2/2015 | Macho et al. |
| 9,008,801 | B2 | 4/2015 | Kaib et al. |
| 9,084,583 | B2 | 7/2015 | Mazar et al. |
| 9,089,685 | B2 | 7/2015 | Sullivan et al. |
| 9,119,547 | B2 | 9/2015 | Cazares et al. |
| 9,131,901 | B2 | 9/2015 | Volpe et al. |
| 9,132,267 | B2 | 9/2015 | Kaib |
| 9,265,432 | B2 | 2/2016 | Warren et al. |
| 9,345,898 | B2 | 5/2016 | Piha et al. |
| 9,408,548 | B2 | 8/2016 | Volpe et al. |
| 9,445,719 | B2 | 9/2016 | Libbus et al. |
| 9,454,219 | B2 | 9/2016 | Volpe et al. |
| 9,579,020 | B2 | 2/2017 | Libbus et al. |
| 9,592,403 | B2 | 3/2017 | Sullivan |
| 9,598,799 | B2 | 3/2017 | Shoshani et al. |
| 9,675,804 | B2 | 6/2017 | Whiting et al. |
| 9,878,171 | B2 | 1/2018 | Kaib |
| 9,895,105 | B2 | 2/2018 | Romem |
| 9,901,741 | B2 | 2/2018 | Chapman et al. |
| RE46,926 | E | 7/2018 | Bly et al. |
| 10,016,613 | B2 | 7/2018 | Kavounas |
| 10,076,656 | B2 | 9/2018 | Dar et al. |
| 10,192,387 | B2 | 1/2019 | Brinig et al. |
| 10,307,133 | B2 | 6/2019 | Kaib |
| 10,463,867 | B2 | 11/2019 | Kaib et al. |
| 10,589,110 | B2 | 3/2020 | Oskin et al. |
| 10,599,814 | B2 | 3/2020 | Landrum et al. |
| 2002/0181680 | A1 | 12/2002 | Linder et al. |
| 2003/0158593 | A1 | 8/2003 | Heilman et al. |
| 2005/0107833 | A1 | 5/2005 | Freeman et al. |
| 2005/0107834 | A1 | 5/2005 | Freeman et al. |
| 2006/0173499 | A1 | 8/2006 | Hampton et al. |
| 2008/0312709 | A1 | 12/2008 | Vollpe et al. |
| 2009/0005827 | A1 | 1/2009 | Weintraub et al. |
| 2010/0007413 | A1 | 1/2010 | Herleikson |
| 2010/0298899 | A1 | 11/2010 | Donnelly et al. |
| 2011/0022105 | A9 | 1/2011 | Owen et al. |
| 2011/0288604 | A1 | 11/2011 | Kaib et al. |
| 2011/0288605 | A1 | 11/2011 | Kaib et al. |
| 2012/0112903 | A1 | 5/2012 | Kaib et al. |
| 2012/0144551 | A1 | 6/2012 | Guldalian |
| 2012/0150008 | A1 | 6/2012 | Kaib et al. |
| 2012/0158075 | A1 | 6/2012 | Kaib et al. |
| 2012/0191476 | A1 | 7/2012 | Reid et al. |
| 2012/0265265 | A1 | 10/2012 | Razavi et al. |
| 2012/0283794 | A1 | 11/2012 | Kaib et al. |
| 2012/0293323 | A1 | 11/2012 | Kaib et al. |
| 2012/0302860 | A1 | 11/2012 | Volpe et al. |
| 2012/0310315 | A1 | 12/2012 | Savage et al. |
| 2013/0085538 | A1 | 4/2013 | Volpe et al. |
| 2013/0144355 | A1 | 6/2013 | Macho et al. |
| 2013/0231711 | A1 | 9/2013 | Kaib |
| 2013/0245388 | A1 | 9/2013 | Rafferty et al. |
| 2013/0274565 | A1 | 10/2013 | Langer et al. |
| 2013/0317852 | A1 | 11/2013 | Worrell et al. |
| 2013/0325078 | A1 | 12/2013 | Whiting et al. |
| 2014/0012144 | A1 | 1/2014 | Crone |
| 2014/0025131 | A1 | 1/2014 | Sullivan et al. |
| 2014/0043149 | A1 | 2/2014 | Cowan et al. |
| 2014/0046391 | A1 | 2/2014 | Cowan et al. |
| 2014/0070957 | A1 | 3/2014 | Longinotti-Buitoni et al. |
| 2014/0085082 | A1 | 3/2014 | Lyon et al. |

(56) References Cited

U.S. PATENT DOCUMENTS

| | | |
|---|---|---|
| 2014/0163334 A1 | 6/2014 | Volpe |
| 2014/0163663 A1 | 6/2014 | Poddar et al. |
| 2014/0296931 A1* | 10/2014 | Chapman ............. A61N 1/3904 607/7 |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0057964 A1* | 2/2015 | Albinali ................. G16H 40/67 702/141 |
| 2015/0161554 A1 | 6/2015 | Sweeney et al. |
| 2015/0297135 A1 | 10/2015 | Shoshani et al. |
| 2015/0328472 A1 | 11/2015 | Sullivan et al. |
| 2016/0004831 A1 | 1/2016 | Carlson et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |
| 2016/0256104 A1 | 9/2016 | Romem et al. |
| 2016/0283900 A1 | 9/2016 | Johnson et al. |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0162840 A1 | 6/2017 | Pendry |
| 2017/0319862 A1 | 11/2017 | Foshee, Jr. et al. |
| 2017/0367591 A1 | 12/2017 | Jorgensen |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2018/0361165 A1 | 12/2018 | Jaax et al. |
| 2019/0030352 A1 | 1/2019 | Sullivan et al. |
| 2019/0076666 A1 | 3/2019 | Medema |
| 2019/0116896 A1 | 4/2019 | Armour et al. |
| 2019/0321650 A1 | 10/2019 | Raymond et al. |

FOREIGN PATENT DOCUMENTS

| | | |
|---|---|---|
| JP | 4320257 A | 3/2005 |
| JP | 5963767 A | 1/2014 |
| JP | 2014526282 A | 10/2014 |
| WO | 98/39061 A2 | 9/1998 |
| WO | 1998039061 A2 | 9/1998 |
| WO | 2011/146448 A1 | 11/2011 |
| WO | 2012/064604 A1 | 5/2012 |
| WO | 2012064604 A1 | 5/2012 |
| WO | 2012/151160 A1 | 11/2012 |
| WO | 2015/056262 A1 | 4/2015 |

OTHER PUBLICATIONS

Klein, H. U., Goldenberg, I., and Moss, A. J., "Risk Stratification for Implantable Cardioverter Defibrillator Therapy: The Role of the Wearable Cardioverter-Defibrillator, Clinical update," European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

Klein, H. U., Goldenberg I., & Moss, A. J., Risk Stratification for Implantable Cardioverter Defibrillator Therapy: The Role of the Wearable Cardioverter-Defibrillator, Clinical update, European Heart Jounal, May 31, 2013, pp. 1-14, doi:10.1093/eurheartj/eht167, European Society of Cardiology.

Heartstart MRx and XL AED Algorithm—Application Note, Jul. 2001, Edition 2 Phillips Healthcare, USA.

Zoll LifeVest Model 4000 Patient Manual PN 20B0047 Rev B, (C) 2009-2012.

Zoll LifeVest® Wear Time Report (2012).

Oyekan, E., Nimalasuriya A, Martin J. et al. The B-SMART Appropriate Medication-Use Process: A Guide for Clinicians to Help Patients—Part 1: Barriers, Solutions and Motivation. The Permanente Journal 2009 (13)1:62-69.

Oyekan, E., Nimalasuriya A, Martin J. et al. The B-SMART Appropriate Medication-Use Process: A Guide for Clinicians to Help Patients—Part 2: Adherence, Relationships and Triage. The Permanente Journal 2009 (13)4:50-54.

* cited by examiner

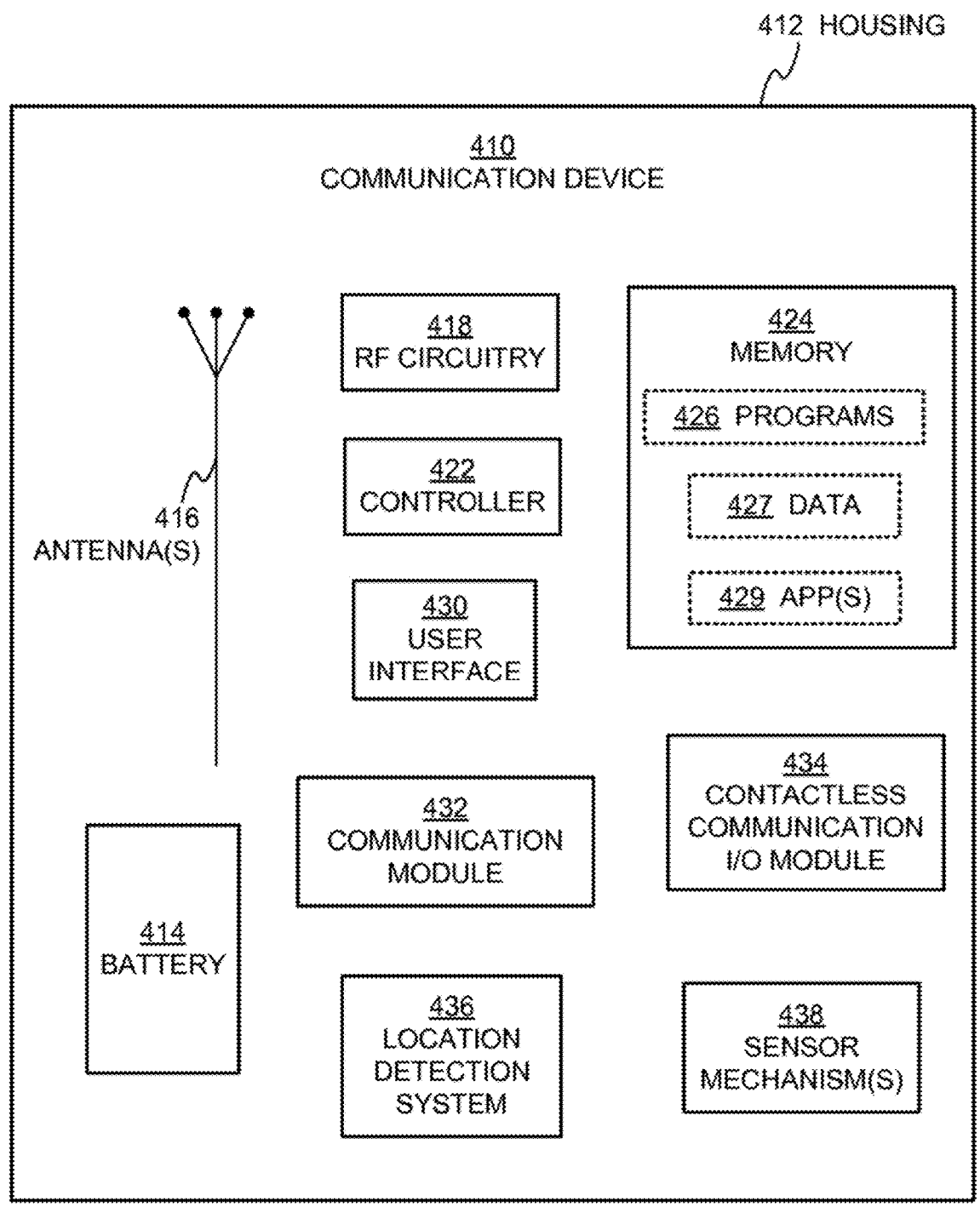
FIG. 4    SAMPLE COMPONENTS

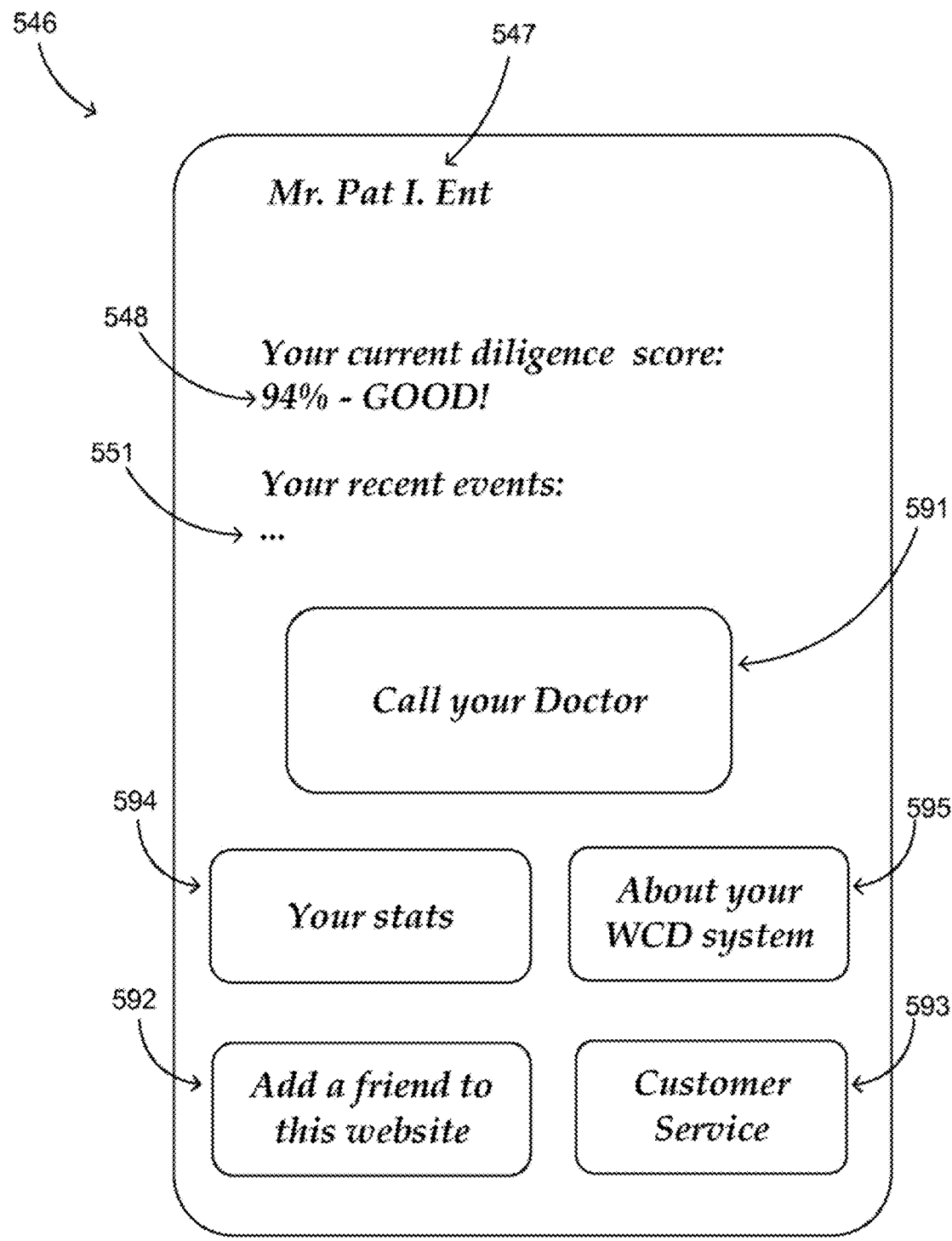
FIG. 5 WEBSITE VIEW

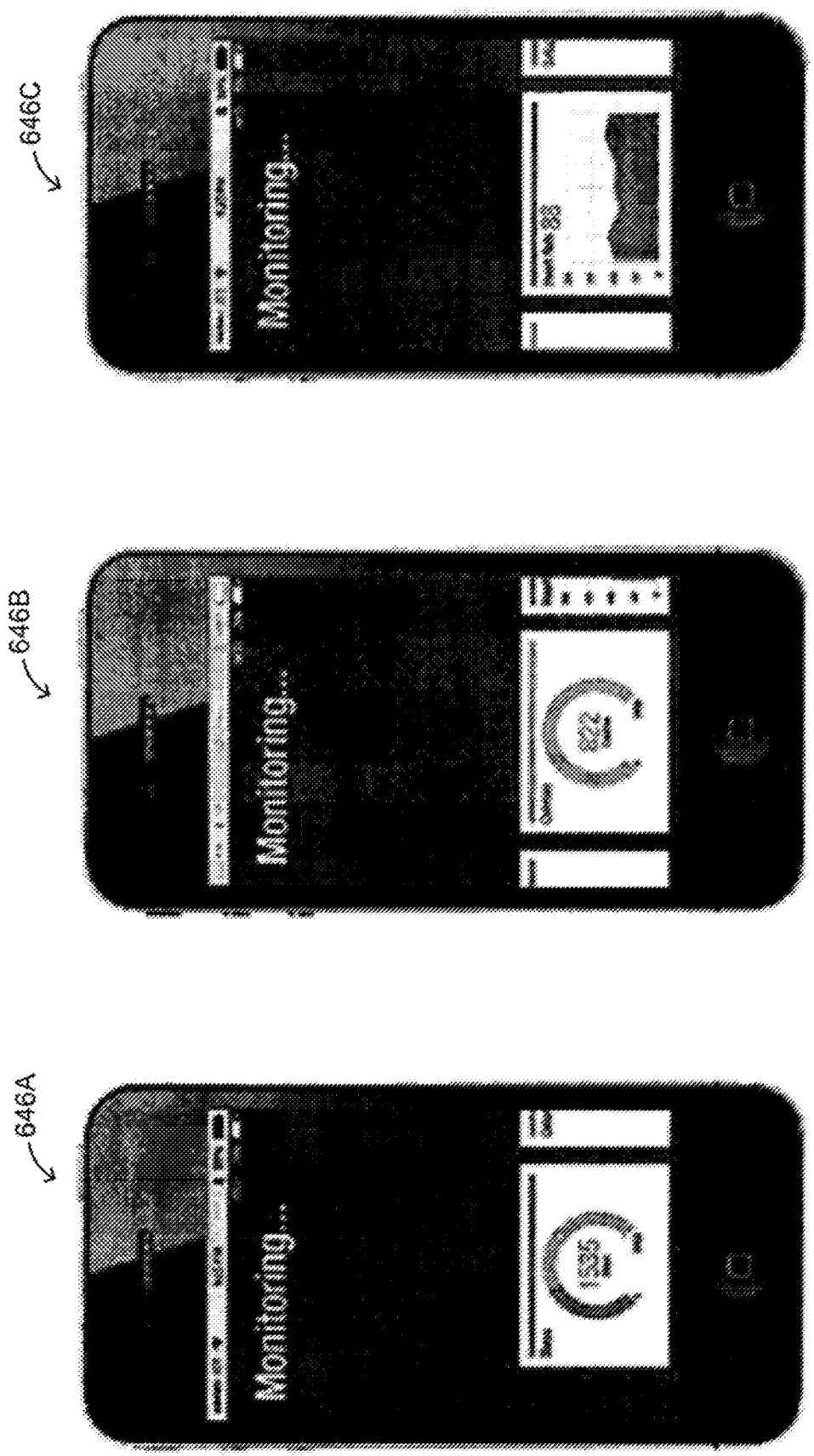

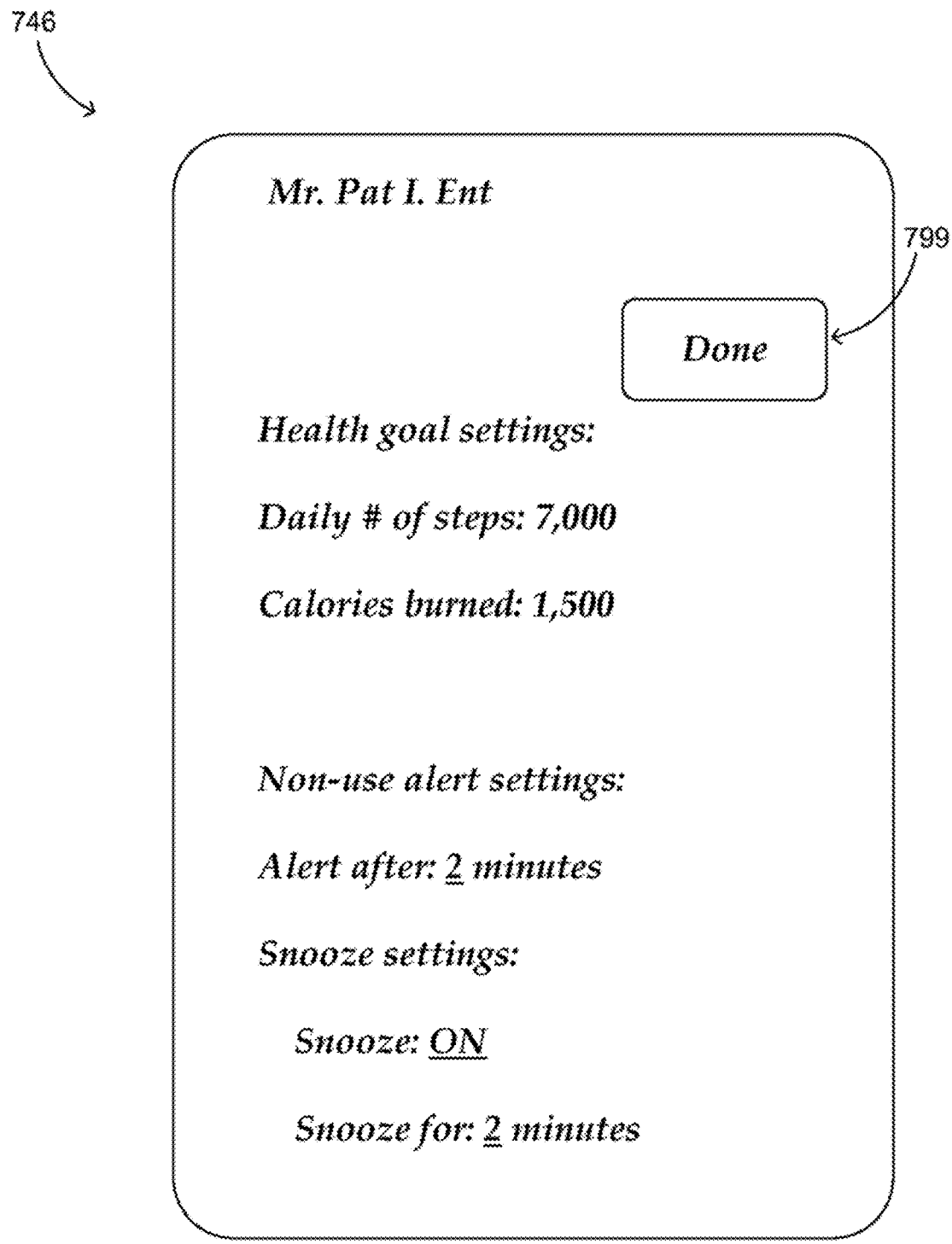
FIG. 7  COMPLIANCE SETTINGS

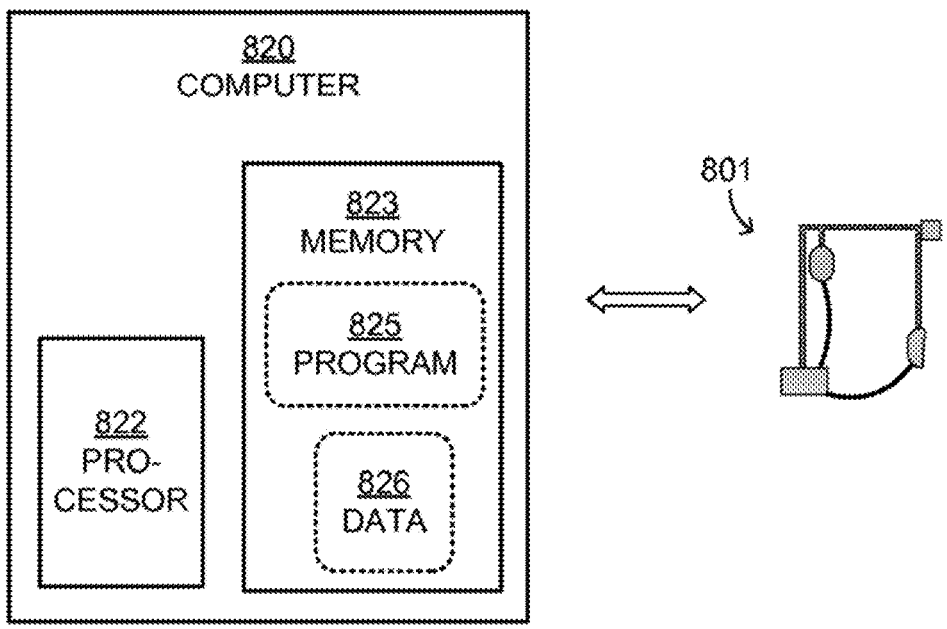
FIG. 8  COMPLIANCE MONITORING
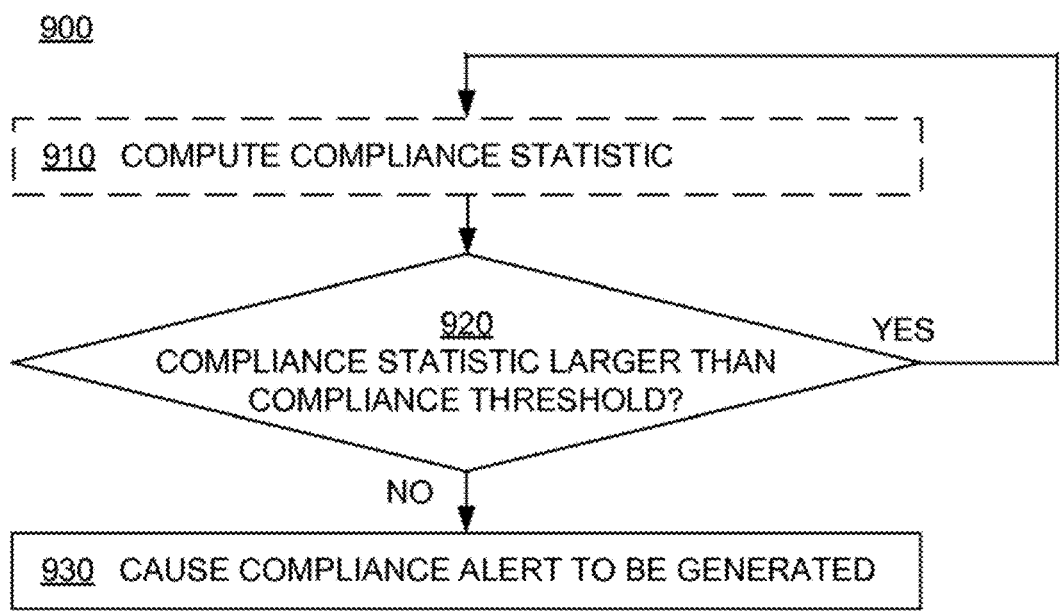
FIG. 9  COMPLIANCE MONITORING > Hello Mrs. Jones – I see that you have worn your WCD for less than 12 hours each of the last three days. Why is that?

> It beeps at me.

> Well, I see that the noise alarms have been sounding many times throughout the day. It this what you mean?

> Yes, I suppose that might be it.

> Well, why don't you come it to my office and we'll see what we can do to fix that.

FIG. 10

ALERTING FOR NON-USE

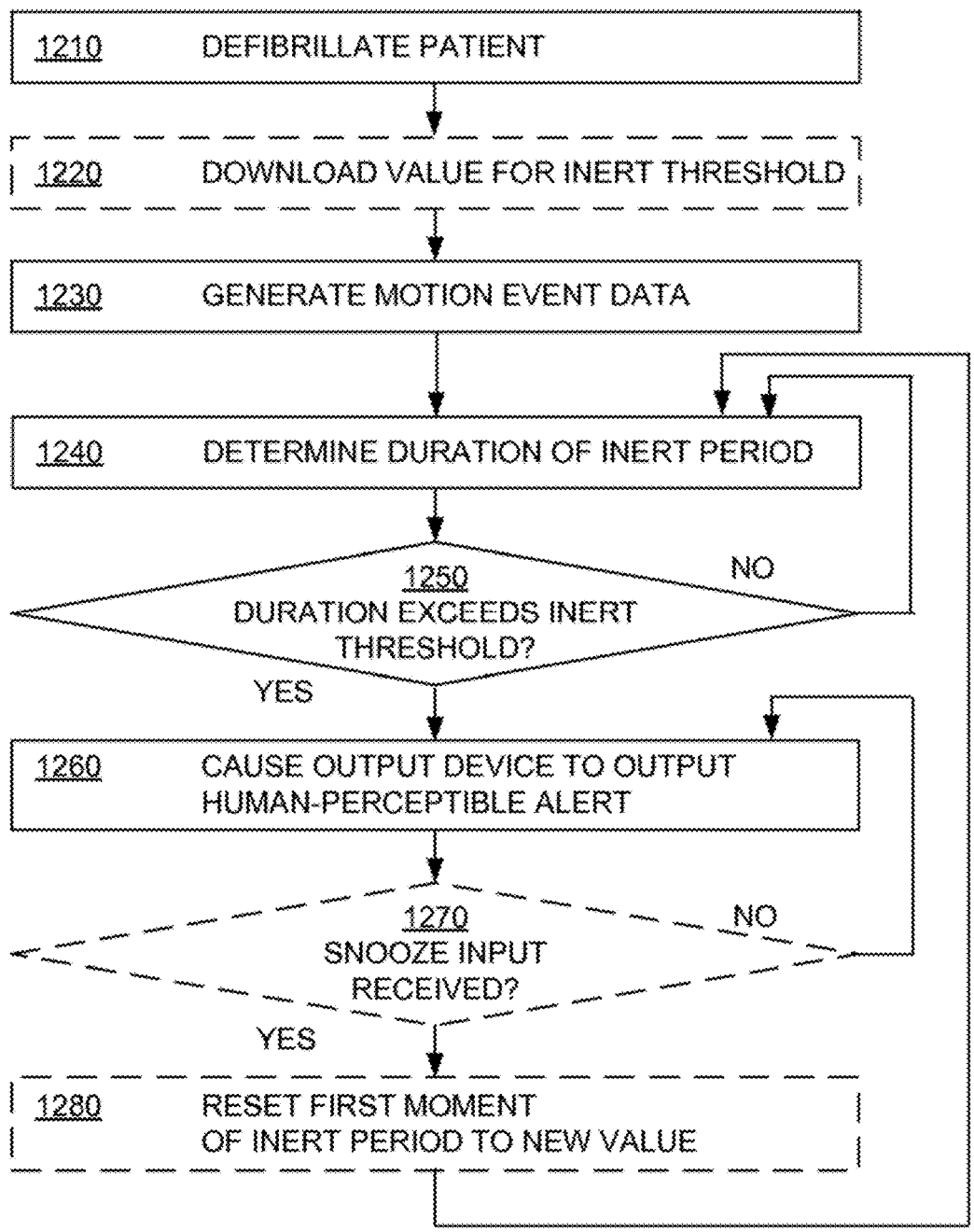
FIG. 12 *METHODS*

NETWORK-ACCESSIBLE DATA ABOUT PATIENT WITH WEARABLE CARDIAC DEFIBRILLATOR SYSTEM

CROSS REFERENCE TO RELATED PATENT APPLICATIONS

This application is a continuation of U.S. patent application Ser. No. 16/593,898, filed Oct. 4, 2019, titled NETWORK-ACCESSIBLE DATA ABOUT PATIENT WITH WEARABLE CARDIAC DEFIBRILLATOR SYSTEM, which is a continuation of U.S. patent application Ser. No. 14/580,183, filed Dec. 22, 2014, now U.S. Pat. No. 10,449,370 issued Oct. 22, 2019, titled NETWORK-ACCESSIBLE DATA ABOUT PATIENT WITH WEARABLE CARDIAC DEFIBRILLATOR SYSTEM, which claims priority from U.S. Provisional Patent Application Ser. No. 61/992,850, filed on May 13, 2014, the disclosures of which are hereby incorporated by reference for all purposes.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim.

Some people have an increased risk of SCA. People at a higher risk include individuals who have had a heart attack, or a prior SCA episode. A frequent recommendation is for these people to receive an Implantable Cardioverter Defibrillator ("ICD"). The ICD is surgically implanted in the chest, and continuously monitors the person's electrocardiogram ("ECG"). If certain types of heart arrhythmias are detected, then the ICD delivers an electric shock through the heart.

After being identified as having an increased risk of an SCA, and before receiving an ICD, these people are sometimes given a wearable cardiac defibrillator ("WCD") system. A WCD system typically includes a harness, vest, or other garment for wearing by the patient. The system includes a defibrillator and external electrodes, which are attached on the inside of the harness, vest, or other garment. When a patient wears a WCD system, the external electrodes may then make good electrical contact with the patient's skin, and therefore can help monitor the patient's ECG. If a shockable heart arrhythmia is detected, then the defibrillator of the WCD system delivers the appropriate electric shock through the patient's body, and thus through the heart.

When a patient is given a WCD system, the prescription is that they wear it continuously, except perhaps when bathing. A challenge is that a patient will often not wear the WCD system, even though it is prescribed. For example, he might neglect to wear it again after bathing.

BRIEF SUMMARY

The present description gives instances of devices, systems, software and methods, the use of which may help a patient with his or her compliance about wearing a wearable cardiac defibrillator (WCD) system that has been assigned to them.

In embodiments, a data file system includes one or more files about a patient wearing a wearable cardiac defibrillator (WCD) system that has been assigned to them. The one or more files may contain at least one patient identifier of the patient, compliance data about a history of the patient's wearing the WCD system, and possibly other data. The data file system can be accessed through a communication network when the patient uses a communication device. When so accessed, some of the contents can be viewed on a screen of the device, for example in the form of a website. In embodiments, the health care provider and friends and family can view such data and even enter inputs, which may create a situation that motivates the patient to comply better.

In embodiments, a wearable cardiac defibrillator (WCD) system that has been assigned to a patient for wearing may include a motion sensor that generates motion event data. A processor may determine, as a proxy for patient generated motion, whether a compliance statistic about the motion event data is larger than a compliance threshold about the patient wearing the WCD system. If not, a compliance alert can be caused to be generated. Accordingly, problems or impediments in the patient's compliance can be detected and be hopefully rectified.

In embodiments, a wearable cardiac defibrillator (WCD) system that has been assigned to a patient for wearing may include a motion sensor that generates motion event data. Inert periods may be determined from a motion statistic of the motion event data. The WCD system may also include a timer, for determining durations of these inert periods. An output device may output an alert if the duration of the inert period exceeds an inert threshold, which may warn about non-use, i.e. non-wearing of the WCD system. In optional embodiments, a snooze feature may be implemented regarding outputting the alert, which may be further disabled.

These and other features and advantages of this description will become more readily apparent from the Detailed Description, which proceeds with reference to the associated drawings in which:

BRIEF DESCRIPTION OF THE DRAWINGS

FIG. 4 is a diagram showing sample components of a communication device that could be the device of FIG. 1, and which is made according to embodiments.

FIG. 5 is a diagram showing a sample image that can be displayed by the screen of a communication device, such as that of FIG. 1, according to embodiments.

FIG. 6 shows sample images of displays by a communication device, such as that of FIG. 1, according to embodiments.

FIG. 7 is a diagram showing a sample image that can be displayed by a communication device, such as that of FIG. 1, according to embodiments.

FIG. 8 is a diagram of a sample computer and a sample associated wearable cardiac defibrillator (WCD) system according to embodiments.

FIG. 9 is a flowchart for illustrating methods according to embodiments.

FIG. 10 shows a possible dialogue, verbal or by text messages, between a patient and an attendant who is monitoring the patient's compliance, and which may result from embodiments.

FIG. 12 is a flowchart for illustrating methods according to embodiments.

DETAILED DESCRIPTION

As has been mentioned, the present description is about devices, systems, software and methods for helping a patient with their compliance about wearing a wearable cardiac defibrillator (WCD) system that has been assigned to them. Embodiments are now described in more detail.

Figure 1:
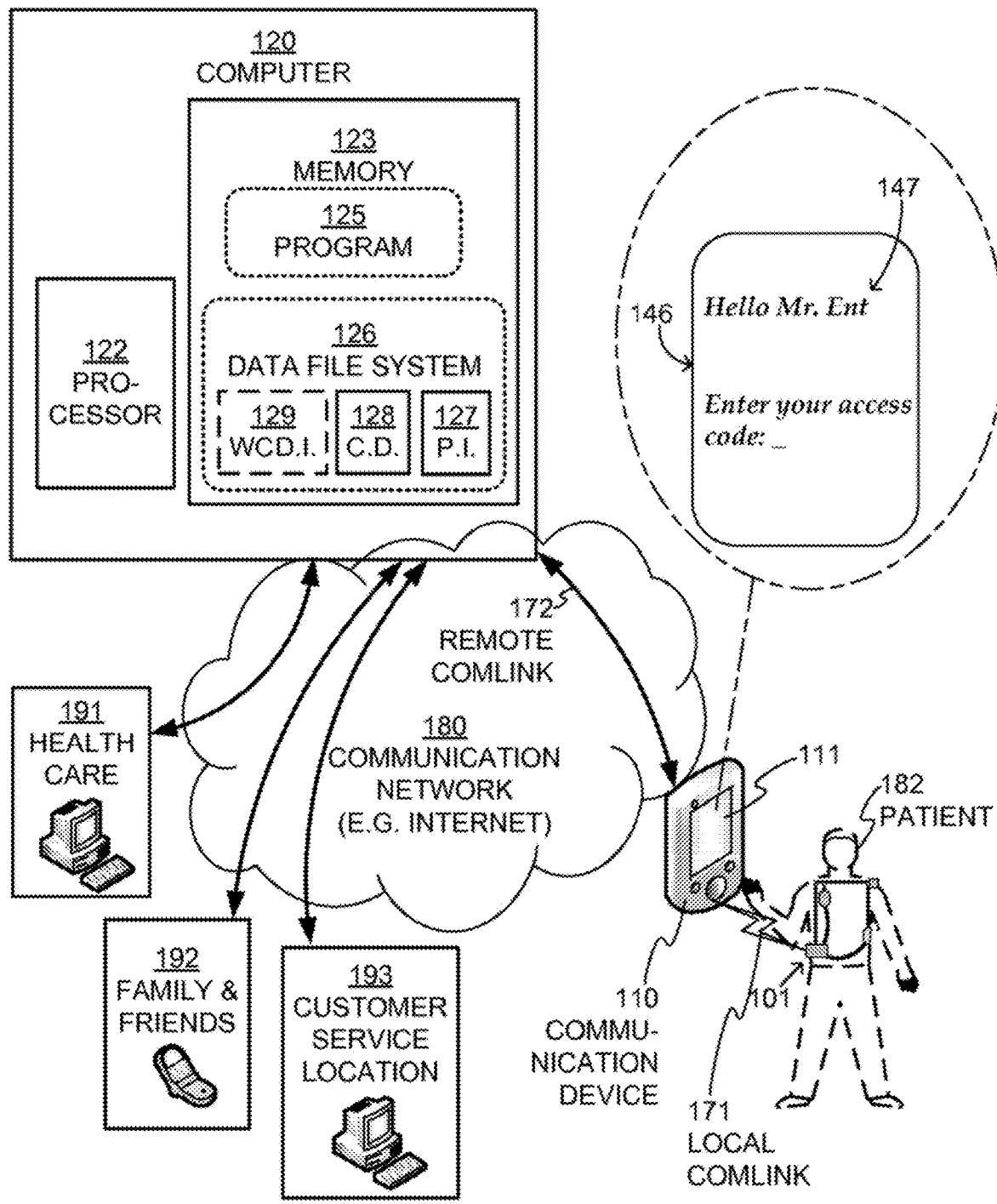
FIG. 1 is a composite diagram of a sample embodiments and arrangements according to embodiments.

FIG. 1 shows a patient 182 wearing a sample wearable cardiac defibrillator (WCD) system 101 made according to embodiments. Patient 182 is also using a communication device 110. Communication device 110 can be either a part of the WCD system, or a commercially available mobile communication device that has one or more suitable applications ("apps") loaded onto it. In the example of FIG. 1, communication device 110 forms a wireless local communication link ("comlink") 171 with the WCD system. In other embodiments, the local comlink can be wired.

In FIG. 1, patient 182 is using communication device 110, while wearing WCD system 101. Before completing the description of the aspects of FIG. 1, WCD system 101 and communication device 110 are now considered in more detail.

Figure 2:
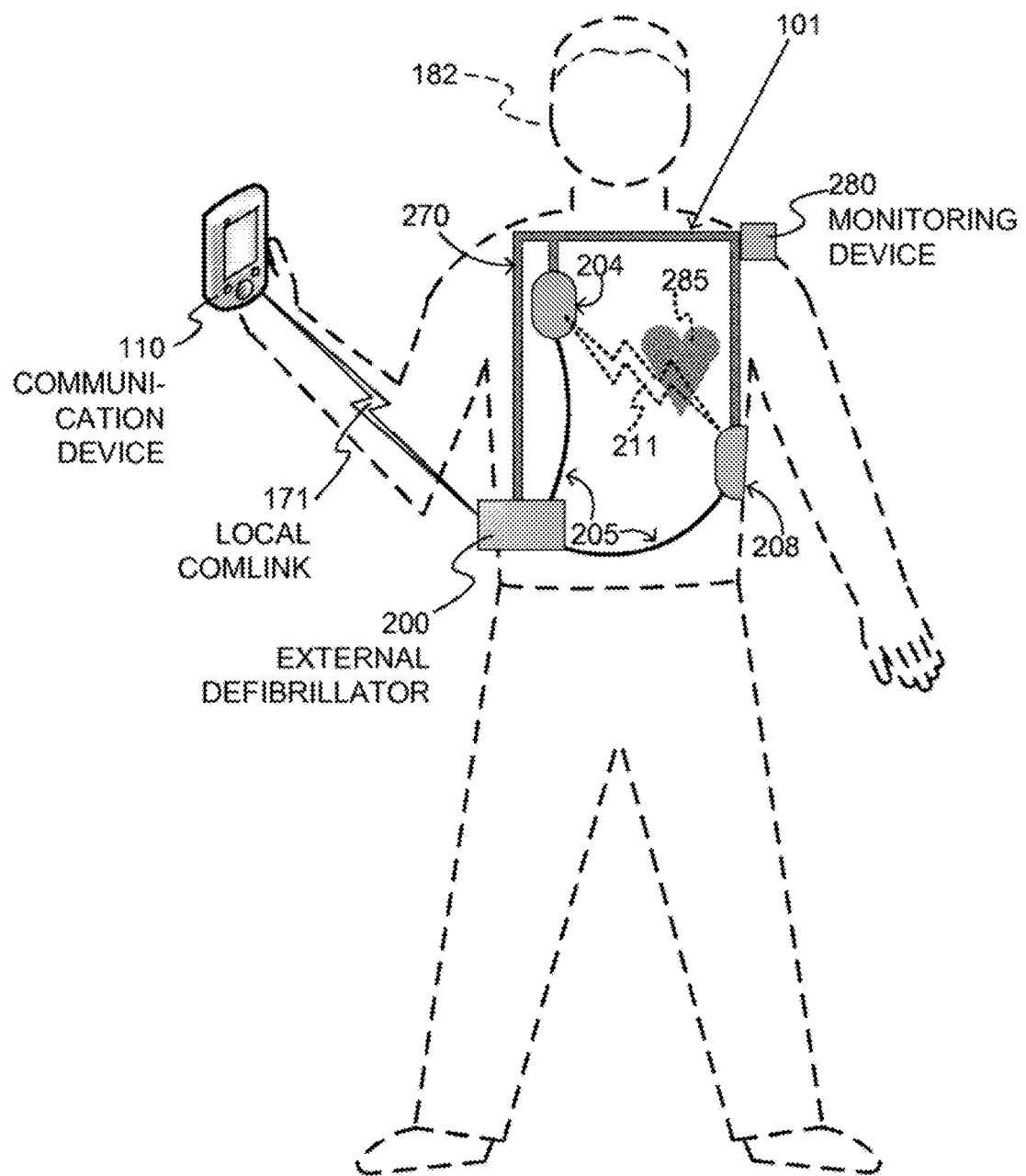
FIG. 2 is a diagram showing a detail of FIG. 1, where a patient wears a sample wearable cardiac defibrillator (WCD) system according to embodiments.

FIG. 2 shows a detail of a portion of FIG. 1 that shows patient 182 wearing wearable cardiac defibrillator (WCD) system 101 and using communication device 110.

WCD system 101 includes a support structure 270 that is configured to be worn by patient 182. Patient 182 is using communication device 110, while wearing support structure 270. WCD system 101 also includes an external defibrillator 200 that is coupled to support structure 270. Defibrillator 200 is configured to defibrillate patient 182 while patient 182 wears support structure 270.

Support structure 270 can be any structure suitable for wearing, such as a harness, a vest, another garment, and so on. The support structure can be implemented in a single component, or multiple components. For example, a support structure may have a top component resting on the shoulders, for ensuring that the defibrillation electrodes will be in the right place for defibrillating, and a bottom component resting on the hips, for carrying the bulk of the weight of the defibrillator. A single component embodiment could be with a belt around the torso, or a harness around the shoulders. Other embodiments could use an adhesive structure or another way for attaching to the patient, with or without encircling any part of the body. There can be other examples.

A generic support structure 270 is shown relative to the body of patient 182, and thus also relative to his or her heart 285. Structure 270 could be a harness, vest, garment, as per the above; it could be implemented in a single component, or multiple components, and so on. Structure 270 is configured to be wearable by patient 182, but the manner of wearing it is not depicted, as structure 270 is depicted only generically in FIG. 2.

WCD system 101 is configured to defibrillate the patient by delivering electrical charge to the patient's body. FIG. 2 shows an example of defibrillation electrodes 204, 208, which are coupled to an external defibrillator 200 via electrode leads 205. When defibrillation electrodes 204, 208 make good electrical contact with the body of patient 182, defibrillator 200 can administer, via electrodes 204, 208, a brief, strong electric pulse 211 through the body. Pulse 211, also known as a defibrillation shock, goes also through heart 285, in an attempt to restart it, for saving the life of patient 182. Defibrillator 200 and defibrillation electrodes 204, 208 are coupled to support structure 270. As such, all components of defibrillator 200 are therefore coupled to support structure 270.

Patient 182 is shown holding communication device 110. Device 110 is shown as having established local comlink 171 with one of the components of WCD system 101. In the example of FIG. 2, local comlink 171 is shown as established specifically with defibrillator 200, on behalf of the entire WCD system 101. This embodiment is advantageous when, as here, defibrillator 200 is collocated with a communication module, but that is not necessary. Indeed, the local comlink can become established with a different component of the WCD system, and particularly the one that includes a wireless communication module on behalf of the entire WCD system.

A prior art defibrillator typically decides whether to defibrillate or not based on an electrocardiogram ("ECG") of the patient. However, defibrillator 200 can defibrillate or not also based additionally on other inputs and received communication, as will be seen later. In addition, the use, readiness and maintenance of defibrillator 200 can be improved based on the communication enabled by the invention.

WCD system 101 may also optionally include a monitoring device 280, which can also be called an outside monitoring device. Monitoring device 280 is configured to monitor at least one local parameter. A local parameter is a parameter of patient 182, or a parameter of the wearable defibrillation system, or a parameter of the environment, as will be described later. Optionally, monitoring device 280 is physically coupled to the support structure. In addition, monitoring device 280 is communicatively coupled with other components coupled to the support structure, such as a communication module, as will be deemed necessary by a person skilled in the art in view of this disclosure.

Figure 3:
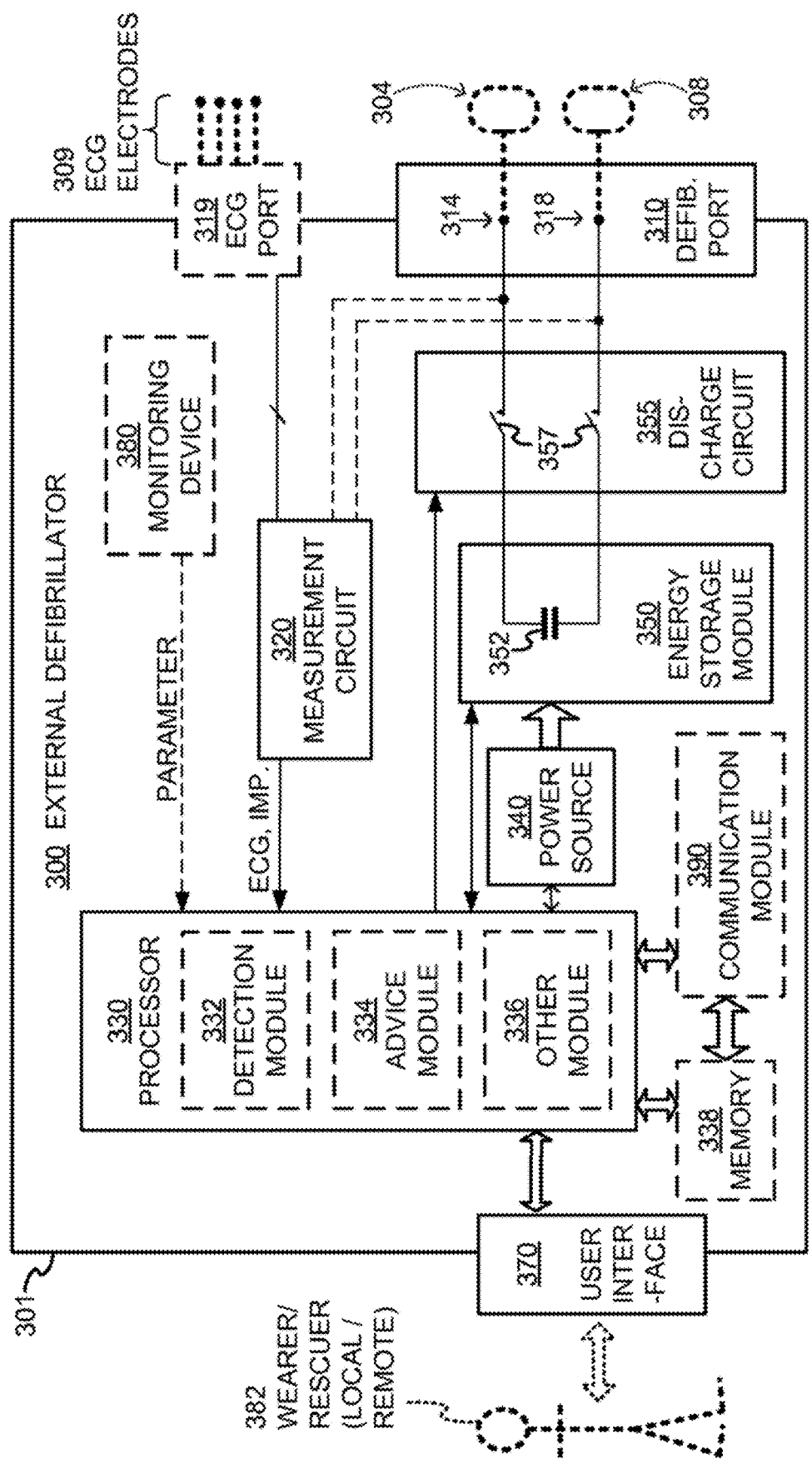
FIG. 3 is a diagram showing components of an external defibrillator, such as the one shown in FIG. 2, and which is made according to embodiments.

FIG. 3 is a diagram showing components of an external defibrillator 300 made according to embodiments. These components can be, for example, in external defibrillator 200 of FIG. 2. The components shown in FIG. 3 can be provided in a housing 301, which is also known as casing 301.

External defibrillator 300 is intended for a patient who would be wearing it, such as patient 182 of FIG. 1 and FIG. 2. Defibrillator 300 further includes a user interface (UI) 370 for a user 382. User 382 can be wearer 182, if conscious. Or user 382 can be a local rescuer at the scene, such as a bystander who might offer assistance, or a trained person. According to FIG. 1, user 382 might be in remote communication with a remote rescuer, such as a trained person within Health Care entity 191, according to embodiments.

Defibrillator 300 may include monitoring device 380 within housing 301, and can also be called an inside monitoring device. Monitoring device 380 can monitor patient parameters, system parameters and/or environmental parameters. In other words, inside monitoring device 380 can be the same, or complementary to outside monitoring device 280 of FIG. 2, and can be provided in addition to it, or instead of it. Allocating which of the whole system parameters are monitored by which monitoring device can be determined according to design considerations. For example, a motion sensor can be within housing 301, as part of inside monitoring device 380, for system economy based on ease of implementation and communicating its results. For another example, a sensor that monitors the patient's blood pressure may be at the external location of device 280.

Defibrillator 300 typically includes a defibrillation port 310, such as a socket in housing 301. Defibrillation port 310 includes nodes 314, 318. Defibrillation electrodes 304, 308, for example similar to electrodes 204, 208 of FIG. 2, can be plugged in defibrillation port 310. Plugging can be from their leads, such as leads 205 of FIG. 2, so as to make electrical contact with nodes 314, 318, respectively. It is also possible that the defibrillation electrodes can be connected continuously to defibrillation port 310, instead. Either way, defibrillation port 310 can be used for guiding, via electrodes, to the wearer the electrical charge that has been stored in energy storage module 350.

Defibrillator 300 may optionally also have an ECG port 319 in housing 301, for plugging in ECG electrodes 309, which are also known as ECG leads. It is also possible that ECG electrodes can be connected continuously to ECG port 319, instead. ECG electrodes 309 can help sense an ECG signal, e.g. a 12-lead signal, or a signal from a different number of leads, as long as they make good electrical contact with the body of the patient. ECG electrodes 309 can be attached to the inside of support structure 270 for making contact with the patient, similarly as the defibrillation electrodes.

Defibrillator 300 also includes a measurement circuit 320. Measurement circuit 320 receives physiological signals from ECG port 319, if provided. Even if defibrillator 300 lacks ECG port 319, measurement circuit 320 can obtain physiological signals through nodes 314, 318 instead, when defibrillation electrodes 304, 308 are attached to the patient. In these cases, a patient's ECG signal can be sensed as a voltage difference between electrodes 304, 308. Plus, impedance between electrodes 304, 308 can be sensed. Sensing the impedance can be useful for detecting, among other things, whether these electrodes 304, 308 are not making good electrical contact with the patient's body. These physiological signals can be sensed, and information about them can be rendered by circuit 320 as data, or other signals, etc.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332. Processor 330, running detection module 332, is a sample embodiment of a logic device configured to determine whether the above-described monitored parameter has reached a specific threshold. For example, the monitoring parameter can be input from monitoring device 380, if provided. For another example, detection module 332 can include a ventricular fibrillation ("VF") detector. The patient's sensed ECG from measurement circuit 320 can be used by the VF detector to determine whether the patient is experiencing VF. Detecting VF is useful, because VF is a precursor to SCA.

Another such module in processor 330 can be an advice module 334, which arrives at advice of what to do. The advice can be based on outputs of detection module 332. There can be many types of advice according to embodiments. As one example, a Shock Advisory Algorithm can render the advice to shock, as opposed to not shock the patient. Such can be, for example, when the patient's condition has reached or exceeded an advised defibrillation threshold. Shocking can be for defibrillation, pacing, and so on.

If the advice is to shock, some external defibrillator embodiments proceed with shocking, or may advise a remote attendant to do it, and so on. As another example, the advice can be to administer CPR, and defibrillator 300 may further issue prompts for it, and so on.

Processor 330 can include additional modules, such as other module 336, for other functions. In addition, if monitoring device 380 is indeed provided, it may be operated in part by processor 330, etc.

Defibrillator 300 optionally further includes a memory 338, which can be a non-transitory computer-readable storage medium. Memory 338 may be able to work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 382, if they are a local rescuer. Moreover, memory 338 can store data. The data can include patient data, system data and environmental data, for example as learned by monitoring device 380 and monitoring device 280. The data can be stored before it is transmitted out of defibrillator 300, or stored after it is received by it.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350, which can be thus be coupled to the support structure of the wearable system. Module 350 is where some electrical energy is stored, when preparing it for sudden discharge to administer a shock. Module 350 can be charged from power source 340 to the right amount of energy, as controlled by processor 330. In typical implementations, module 350 includes a capacitor 352, which can be a single capacitor or a system of capacitors, and so on. As described above, capacitor 352 can store the charge for delivering to the patient.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Sounds, images, vibrations, and anything that can be experienced by user 382 can also be called human perceptible indications. Interface 370 may additionally include various controls, such as pushbuttons, keyboards, touchscreens, a microphone, and so on. In addition, discharge circuit 355 can be controlled by processor 330, or directly by user 382 via user interface 370, and so on.

Defibrillator 300 can optionally include a communication module 390, for establishing one or more wireless comlinks, such as local comlink 171. The communication module may also include an antenna, portions of a processor, and other sub-components as may be deemed necessary by a person skilled in the art. This way, data and commands can be communicated, such as patient data, episode information, therapy attempted, CPR performance, system data, environmental data, and so on. Communication module 390 may also establish a bypass comlink, as described elsewhere in this document.

Defibrillator 300 can optionally include other components.

Returning to FIG. 2, communication device 110 can be a wireless telephone, a smartphone, a Personal Digital Assistant (PDA), a personal electronic device, a pager, a laptop computer, a tablet, an e-reader, and so on. Such communication devices are increasingly becoming more than just wireless voice communication devices. In addition to handling voice data, some communication devices are essentially portable computing devices that can support a variety of applications such as email, web browsing, text processing applications, contact applications, scheduling applications, games, and so on.

Patient 182 typically carries communication device 110, and is intended to be its primary user. Patient 182 may carry device 110 in a pocket, in a special holder, or even wear it on their wrist. It should be further remembered that, given the particular dynamics of SCA, where the patient may be an unconscious victim, a rescuer may actually use the patient's communication device 110. And, in some embodiments, a rescuer may instead use their own communication device, instead of the one carried by the patient.

FIG. 4 is a diagram showing possible sample components of a communication device 410 made according to embodiments. Device 410 could be the same as device 110 that is depicted in FIG. 1. Communication device 410 is typically provided with a housing 412, and its components are typically within housing 412. Device 410 is typically powered by a battery 414 that can be rechargeable. Battery 414 enables device 410 to be portable, mobile.

Communication device 410 includes one or more antennas 416 for wireless communication. Device 410 also includes RF (radio frequency) circuitry 418. RF circuitry 418 cooperates with antenna(s) 416 to receive and send RF signals. RF circuitry 418 converts RF signals to/from wired electrical signals. RF circuitry 418 may include well-known circuitry for performing these functions, including but not limited to an RF transceiver, one or more amplifiers, a tuner, one or more oscillators, a digital signal processor, a CODEC chipset, a subscriber identity module (SIM) card, a memory, and so forth. The one or more antennas 416, plus RF circuitry 418, can establish wireless communication links ("comlinks") as per the above, when cooperating with one of the communication modules of communication device 410 that are described below.

Communication device 410 additionally includes a controller 422, for controlling its operation. Controller 422 can be one or more processors, implemented as a Central Processing Unit (CPU), a digital signal processor, a microprocessor, a microcontroller, an application-specific integrated circuit (ASIC), a programmable logic device (PLD), or other implementation. Controller 422 can be optionally combined in a single chip with a memory controller and a peripherals interface.

Device 410 also includes a memory 424, which can be a non-transitory computer-readable storage medium. Memory 424 can include both persistent/non-volatile and non-persistent/volatile memory components. Memory 424 can be implemented in any technology for memory for such devices, volatile memory, non-volatile memory (NVM), for example RAM, ROM, EEPROM, flash memory, and so on. As such, memory 424 can include a non-transitory computer-readable storage medium. Additional memory components may be plugged in from a device external to housing 412, such as a thumb drive, in some embodiments. Memory 424 can store programs 426 and data 427. Programs 426 can include instructions that can be executed by controller 422. Programs 426 may include an operating system, such as, for example, Android, iOS, Windows Phone, Symbian, or BlackBerry OS.

In addition, one or more applications [app(s)] 429 can be stored in memory 424, as mentioned above. App(s) 429 can also include instructions that can be executed by controller 422. Common app(s) 429 can be provided for a contacts module, an email client module, a calendar module, a camera module, a maps module, and so on.

It will be appreciated that many of the methods of the invention can be performed by communication device 410 due to one or more special app(s) 429, which are provided in addition to common apps. Even if communication device 410 is initially provided in a more generic form without special app(s) 429, the latter may be downloaded later.

Communication device 410 further includes a user interface 430, for use by a user, such as patient 182. User interface 430 includes individual devices for receiving inputs by the user, output devices for generating outputs for the user, or both. The outputs for the user can be human-perceptible indications, such as sounds, vibrations, lights, images, and so on. Examples of such individual devices include a screen that could be a touch screen, a physical keypad, an optical finger interface, one or more speakers, one or more microphones, one or more accelerometers, and so on. Such devices can be included within housing 412, or can be added by a separate plugin, such as a keypad, a keyboard, a display, and a speaker.

Communication device 410 moreover includes a communication module 432. Module 432 can conduct communication using any one of a variety of standards, protocols and technologies. Examples of the latter are Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS), and/or Short Message Service (SMS), or any other suitable communication protocol, including communication protocols not yet developed as of the filing date of this document.

Additionally, communication device 410 can include a contactless communication I/O module 434. Module 434 can be used for short range detection and communication, such as Near-Field Communications (NFC), Radio Frequency Identification (RFID), and so on.

Communication device 410 can also include a location detection system 436, which can be implemented with GPS. Device 410 can further include one or more sensor mechanisms 438. Mechanisms 438 can include one or more accelerometers, a proximity sensor, a magnetometer, optical sensors, an image sensor, and so on. Data captured by location detection system 436 and sensor mechanisms 438 can be stored as data 427.

Programs 426, and also app(s) 429, can advantageously coordinate their use with components of device 410. For example, and depending on the application, antenna(s) 416 may be used to detect electromagnetic fields (EMF), and a microphone of user interface 430 may be used to detect sound. Many of the components of a communication device are well known in the field, and therefore and are not described further.

Returning to FIG. 1, communication device 110 has a screen 111. Screen 111 can be part of user interface 430. A sample view 146 of what can be displayed on screen 111 is shown in a balloon. The contents of view 146 may depend on the communication arrangements, which are now described in more detail.

A communication network 180 can be the internet. Communication device 110 can communicate via communication network 180, for example according to shown arrows. Communication device 110 may exchange data via a remote comlink 172, local comlink 171, or bypass comlinks, for example as described in U.S. Pat. No. 8,838,235 B2, which is incorporated herein by reference.

FIG. 1 additionally shows a computer 120 made according to embodiments. Computer 120 is remote with respect to patient 182; in fact, computer 120 may be accessed via communication network 180 by patient 182 using communication device 110. Access can be via remote comlink 172, which is different from local comlink 171. Comlink 171 may also be through a network, but is it across a smaller distance than comlink 172.

Computer 120 may include a processor 122. Processor 122 may be programmable for a general purpose, or dedicated, such as a microcontroller, a microprocessor, a Digital Signal Processor (DSP), etc.

Computer 120 may also include non-transitory computer-readable storage media, such as at least one memory 123. Memory 123 can be of different types, including but not limited to volatile memory, non-volatile memory (NVM), read only memory (ROM); random access memory (RAM); magnetic disk storage media; optical storage media; smart cards, flash memory devices, etc.

These storage media may store at least one program 125 that processor 122 may be able to read, and execute. More particularly, program 125 can contain instructions in the form of code, which processor 122 may be able to execute upon reading. Executing is performed by physical manipulations of physical quantities, and may result in functions, processes, actions and/or methods to be performed according to embodiments, and/or processor 122 to cause other devices or components or blocks to perform such functions, processes, actions and/or methods. Often, for the sake of convenience only, it is preferred to implement and describe a program as various interconnected distinct software modules or features. These, along with data are individually and also collectively known as software. In some instances, software is combined with hardware, in a mix called firmware.

In addition, these storage media, individually or in combination with others, can have stored thereon data. In the example of FIG. 1, memory 123 may store a data file system 126. Data file system 126 is thus stored in connection with patient 182 having been assigned WCD system 101.

Data file system 126 may include one or more files. These one or more files may contain at least one patient identifier P.I. 127 of the patient, and compliance data C.D. 128 about a history of patient 182 wearing the support structure of WCD system 101.

Data file system 126 can be configured to be accessed via communication network 180 by a person using a communication device, such as patient 182 using communication device 110. Data file system 126 can be accessed this way if computer 120 is a server accessible from the internet, etc.

When data file system 126 is so accessed, patient identifier 127 and compliance data 128 can be configured to be downloaded via communication network 180 to communication device 110. In such cases, screen 111 can be configured to display viewable data about the downloaded patient identifier 127 and about the downloaded compliance data 128. In the example of FIG. 1, sample view 146 includes viewable data 147 about the downloaded patient identifier 127, which are the patient's name.

The viewable data may be displayed in a number of ways. For example, communication device 110 may have a browser application, and the viewable data can be displayed via the browser application. In some embodiments, one or more of the files of data system 126 are provided in html, which makes it easy to display in a browser application.

Data file system 126 may contain additional information. Some of it may be downloadable, and some of that may be further viewable on screen 111. For example, the one or more files optionally further contain at least one WCD identifier 129 of WCD system 101. In some of these embodiments, the viewable data includes data about WCD identifier 129.

In some embodiments access to data file system 126 is protected. For example, using the communication device may include entering an access code. The downloading can be performed responsive to entering the access code. The entered code has to be validated as correct, and so on. Different parties that may access data file system 126 may have different codes, and so on. In some embodiments, the access code is legible on the WCD system, having been written on it in advance. In the example of FIG. 1, a request is shown within view 146 to enter an access code.

Referring now also to FIG. 5, a sample view 546 is shown, which could be the image displayed by communication device 110. View 546 could be, for instance, the view after a correct access code has been entered responsive to view 146 of FIG. 1. In this case, then, view 546 includes viewable data 547, which can be the full name of patient 182.

As mentioned previously, viewable data can be displayed about the downloaded compliance data 128. In the example of FIG. 5, viewable data 548 is compliance data about the compliance of patient 182 actually wearing WCD system 101. For purposes of interacting with patient 182, the term "diligence" may be used to discuss what is, from the clinical point of view, their compliance.

In the example of FIG. 1, viewable data 548 is a percentage score. This score could be, for example, the wear time over the total time over a period spanning back 7 days. It is possible that patient 182 would have to remove WCD system 101 for bathing, which could prevent this percentage score from being maintained at 100.0%.

Returning to FIG. 1, compliance data 128 may be generated in a number of ways. For example, and as mentioned previously, WCD system 101 may further include a motion sensor. The motion sensor can be configured to generate motion event data. The patient's compliance may be inferred from the motion event data, among other factors. For instance, it could be that the motion event data indicates no motion events, and that could be due to the fact that patient 182 is not wearing system 101, and so on.

Another factor for the patient compliance can be the time, for example expecting different motion patterns during the night, accounting for vibrations that can be ruled out as not being patient generated, and so on. As such, the time itself might help interpret the motion event data. One more factor can be as to whether the ECG is received, which speaks to compliance as to wearing system 101 properly or not, and so on.

The motion event data may be communicated in any number of ways. For example, WCD system 101 may include the previously mentioned communications module, which can be configured to communicate the motion event data. Or, communication device 110 can be configured to communicate the motion event data. In such cases, the compliance data can become updated compliance data, responsive to the communicated motion event data. In particular, as current motion event data and other data becomes known and integrated with earlier such data, compliance data 128 may become updated compliance data by adding data, computing updated averages, and so on.

Returning to FIG. 5, view 546 can further include viewable data 551, which can be about relevant recent events. It will be understood that, in such embodiments, the files of the data system can contain such events; when downloaded, these can become viewable data 551.

A number of such events are possible. An important such event can be defibrillation, when it happens. For example, external defibrillator 200 may defibrillate patient 182, and a processor of WCD system 101 can be configured to generate defibrillation event data about the defibrillating. In such instances, the defibrillation event data can be communicated, whether to computer 120 or to another functionality.

Again, communicating the defibrillation event data can be performed in a number of ways. In embodiments, the WCD system further includes a communications module configured to communicate the defibrillation event data. In other embodiments, the communication device is configured to communicate the defibrillation event data.

Once the defibrillation event data is communicated, the one or more files of the data file system can become updated in response to it. This can be performed in a number of ways. For example, the one or more files can become updated so that they contain the defibrillation event data itself. In some embodiments, then, viewable data 551 further includes the defibrillation event data.

Other data can be included, for example alerts, thresholds, and statistics, any of which can be contained in the one or more files. Examples are now described.

In some embodiments, WCD system 101 further includes an energy storage module that stores an electrical charge. In these embodiments, the one or more files of data file system 126 may further contain a battery alert, if an amount of the stored charge is less than a threshold charge. In some embodiments, the battery alert may be generated by WCD system 101 and be communicated to data file system 126. In other embodiments, the amount of charge may be communicated to data file system 126, and the battery alert may be generated within computer 120. In some embodiments, the viewable data further includes the battery alert.

In some embodiments, a compliance statistic is computed about the updated compliance data, as is also described later with reference to FIG. 8. In addition, a compliance alert may be generated if the compliance statistic is not larger than a compliance threshold. In such embodiments, the one or more files may further contain the compliance alert. This alert may also be communicated to an attendant, such as with a Health Care entity 191.

Other included data can be records of such alerts, statistics about such alerts, statistics about compliance history, etc.

View 546 can further include buttons, or equivalent ways to see other views, for example by linking to other webpages or places in network 180. Such a button can be actuated by touching, if the screen is a touchscreen. Examples of such buttons are now described.

In FIG. 5, a button 591 can be for calling a doctor. Actuating it may call Health Care entity 191, seen in FIG. 1. In embodiments, Health Care entity 191 may be able to also download data file system 126, have the same views as patient 182 has with device 110, and so on.

In FIG. 5, a button 592 can be for adding a friend or a family member to the website. Actuating it may enable a family members and friends 192, seen in FIG. 1, to also have access to data file system 126, or selected parts of it, such as the compliance score. The engagement and participating of family members and friends 192 and friends can motivate patient 182, to improve compliance. In embodiments, family members and friends 192 may even enter inputs, such as encouraging notes. Of course, such access to others is preferably granted after patient 182 has voluntarily agreed to waive their confidentiality as to these others, which sometimes can be performed in exchange for signing Non-Disclosure Agreements.

In FIG. 5, a customer service button 593 can be displayed on the screen. The one or more files of data file system 126 may further contain a customer service network address of a customer service location 193 in communication network 180. In such embodiments, actuating the customer service button can accesses the customer service network address.

In FIG. 5, a stats button 594 can be displayed on the screen. Button 594 can be for the patient's information, such as activity information, physiological information, health goals, and related statistics. There can be a number of such types of information. Examples are now described.

FIG. 6 shows sample views 646A, 646B, 646C with viewable data of the patient. In view 646A, the viewable data is activity monitoring in terms of steps walked. In view 646B, the viewable data is metabolic monitoring, in terms of calories burned. In view 646C, the viewable data is heart rate monitoring. In these examples, these views are shown with reference to health goals. In some embodiments the health goals can be adjusted, as is now described.

FIG. 7 shows a sample view 746, which can be reached in a number of ways. One such way is from a button of views 646A, 646B. View 746 permits changing the health goals. In some of these embodiments, these settings are not stored only on communication device 110, but the one or more files of data files system 126 further contain at least one health goal of patient 182. In some of those embodiments, the viewable data includes data about the health goal, for example showing the goal as a graph, a statistic, etc., for example as seen in the views 646A, 646B, 646C of FIG. 6. This data may have thus been downloaded.

View 746 further permits changing settings of the optional non-use alert and snooze features that are described later in this document. Again, in some of these embodiments, these settings are not stored only on the communication device 110, but the one or more files of data files system 126 further contain at least one snooze setting such as the inert threshold. In some of those embodiments, the viewable data includes data about the inert threshold, for example showing its value, as it may have been downloaded.

In view 746, a Done button 799 can take the viewer back to the previous view that they came from.

Returning to FIG. 6, the viewable data that generate views 646A, 646B, 646C can be stored also in data file system 126. In such embodiments, others can also see it, such as Health Care entity 191 and family and friends 192. It will be understood that, in such embodiments, the files of data file system 126 can contain the patient information which, when downloaded, becomes the viewable data of views 646A, 646B, 646C.

An example of the type of patient information that can be contained in the files of data file system 126 is patient physiological data. For example, WCD system 101 can further include a measurement circuit configured to generate patient physiological data from a patient physiological signal. In such instances, the patient physiological data can be communicated, whether to computer 120 or to another functionality.

Again, communicating the patient physiological data can be performed in a number of ways. In embodiments, the WCD system further includes a communications module configured to communicate the patient physiological data. In other embodiments, the communication device is configured to communicate the patient physiological data.

Once the patient physiological data is communicated, the one or more files of the data file system can become updated in response to it, etc. In some embodiments, then, the viewable data further includes the patient physiological data.

Returning to FIG. 5, an education button 595 can be displayed on the screen. Education button 595 can be labeled as shown, and show information about WCD system 101, access system settings, and so on. For example, an information location in a communication network may include information about WCD system 101. This information location can be a help website set up by the manufacturer, etc. The one or more files of data file system 126 further contain an information network address of the information location in network 180. Actuating the education button may access the information network address.

Embodiments of the invention are also intended to facilitate monitoring compliance of a patient wearing a wearable cardiac defibrillator (WCD) system that has been assigned to him. These embodiments are now described in more detail.

FIG. 8 is a diagram of a computer 820 and an associated WCD system 801 according to embodiments. As with WCD system 101, WCD system 801 includes a support structure which is configured to be worn by a patient such as patient 182. WCD system 801 also includes an external defibrillator coupled to the support structure. Additionally, WCD system 801 may include a motion sensor coupled to the support structure and configured to generate motion event data. Moreover, and as described above, WCD system 801 may include a communication module and/or the patient wearing WCD system 801 may use a communication device.

Computer 820 includes a processor 822, which can be made as was described for processor 122. Computer 820 also includes a non-transitory storage medium 823, which is also known as memory 823 and can be as memory 123. Memory 823 can be coupled with processor 822, and store one or more programs 825 and data 826.

In FIG. 8, computer 820 is associated with WCD system 801 in the sense that the one or more programs 825 are stored in connection with a patient having been assigned to wear WCD system 801. This may be performed in a number of ways. In some types of embodiments computer 820 is remote from WCD system 801, for example as computer 120 is with respect to WCD system 101. In these types of embodiments, computer 820 can be called a remote computer, even though a remote comlink between them can be over a short physical distance, such as using Bluetooth. In other types of embodiments, computer 820 is actually part of system 801. Common aspects of both types of embodiments are described first.

Methods and algorithms are also described below. These methods and algorithms are not necessarily inherently associated with any particular logic device such as computer 120 or 820, or their components, or other apparatus such as a WCD system. As such, they can be implemented by programs 125, 825 or other programs for use by a computing machine, such as a general-purpose computer, a special purpose computer, a microprocessor; they can be the result of such programs being executed by such a processor, etc., for solving specific problems in specific contexts.

This detailed description includes flowcharts, display images, algorithms, and symbolic representations of program operations within at least one computer readable medium. An economy is achieved in that a single set of flowcharts is used to describe both programs, and also methods. So, while flowcharts describe methods in terms of boxes, they also concurrently describe programs.

FIG. 9 shows a flowchart 900 for describing methods according to embodiments. The methods of flowchart 900 may also be practiced by embodiments described above.

According to an optional operation 910, a compliance statistic is computed. The compliance statistic can be about motion event data generated by the motion detector of WCD system 801.

According to another operation 920, it can be determined whether the compliance statistic is larger than a compliance threshold. The compliance threshold can be about the patient wearing the support structure, for example for how long a time. If the answer is yes, the execution can return to operation 910. Moreover, additional motion event data may be received, operation 910 can yield an updated compliance statistic, and so on.

If the answer for operation 920 is no, then according to another operation 930, a compliance alert can be caused to be generated. This may be received by an attendant, who may communicate with the patient. Their dialogue can be, for example, as shown in FIG. 10.

Examples of the types of embodiments that are as in FIG. 1 are now described.

In some of these embodiments, operation 910 is not performed by the processor. Rather, WCD system 801 may compute the compliance statistic, which can then be communicated to the remote processor.

In some of these embodiments, operation 910 is performed by the processor. In particular, WCD system 801 can communicate the motion event data via a communication network to the remote processor. Then the compliance statistic can be computed from the motion event data. In some instances, the remote computer further includes a timer, which is configured to generate a time signal. In such instances, the compliance statistic can be computed also from the time signal.

In some of these embodiments, the remote computer further includes an output device, which can be part of a user interface. In addition to the operations of flowchart 900, when the programs are executed by the processor, they can cause the compliance alert to be communicated via the output device. The output device may produce a visual or auditory signal, so as to attract the attention of the attendant.

In some of these embodiments, the compliance threshold can be adjusted. Adjustment can be by any of the parties involved, although it is advisable to restrict access to perhaps only the attendant. In some such instances, therefore, in addition to the operations of flowchart 900, an adjustment input can be received. Then, when the programs are executed by the remote processor, they may further result in adjusting the compliance threshold, responsive to the received adjustment input.

Referring to FIG. 8, examples are now described of the types of embodiments where computer 820 is part of WCD system 801. In such embodiments, computer 820 need not be a standalone aspect of WCD system 801, but the components of computer 820 may be implemented within WCD system 801. In some of these embodiments, for example, processor 822 can be as processor 330, i.e. within the external defibrillator. When the programs are executed by the processor, they may thus further result in defibrillating the patient while the support structure is worn by the patient.

In many of these embodiments, WCD system 801 further includes a communication module. Different elements can be caused to be communicated by the communication module. In some of these embodiments, the motion event data is caused to be communicated by the communication module.

In some of these embodiments, the compliance statistic is computed from the motion event data, as per operation 910. Then the compliance statistic can be caused to be communicated by the communication module. In some instances, WCD system 801 further includes a timer, which is configured to generate a time signal. In such instances, the compliance statistic can be computed also from the time signal.

In some of these embodiments, the generated alert is communicated by the communication module.

A method for WCD system 801 may include the operations of flowchart 900, plus defibrillating the patient while the support structure is worn by the patient. In addition, if WCD system 801 further includes a communication module, different elements can be caused to be communicated by it as described above.

Embodiments of the invention further include alerting for non-use of a wearable cardiac defibrillator system. Referring, for example, to FIG. 2, a wearable cardiac defibrillator (WCD) system according to embodiments could be such as WCD system 101, which includes support structure 270 and external defibrillator 200. Such as WCD system can additionally include a motion sensor coupled to the support structure and configured to generate motion event data. Such as WCD system can further include a timer coupled to the support structure, and configured to determine a duration of an inert period. The inert period can be a period during which a motion statistic of the motion event data is less than a motion threshold. If the duration of the inert period exceeds an inert threshold, then an output device can be configured to output a human-perceptible alert for non-use. The output device can be part of a user interface, and so on. Particulars are now described.

Figure 11:
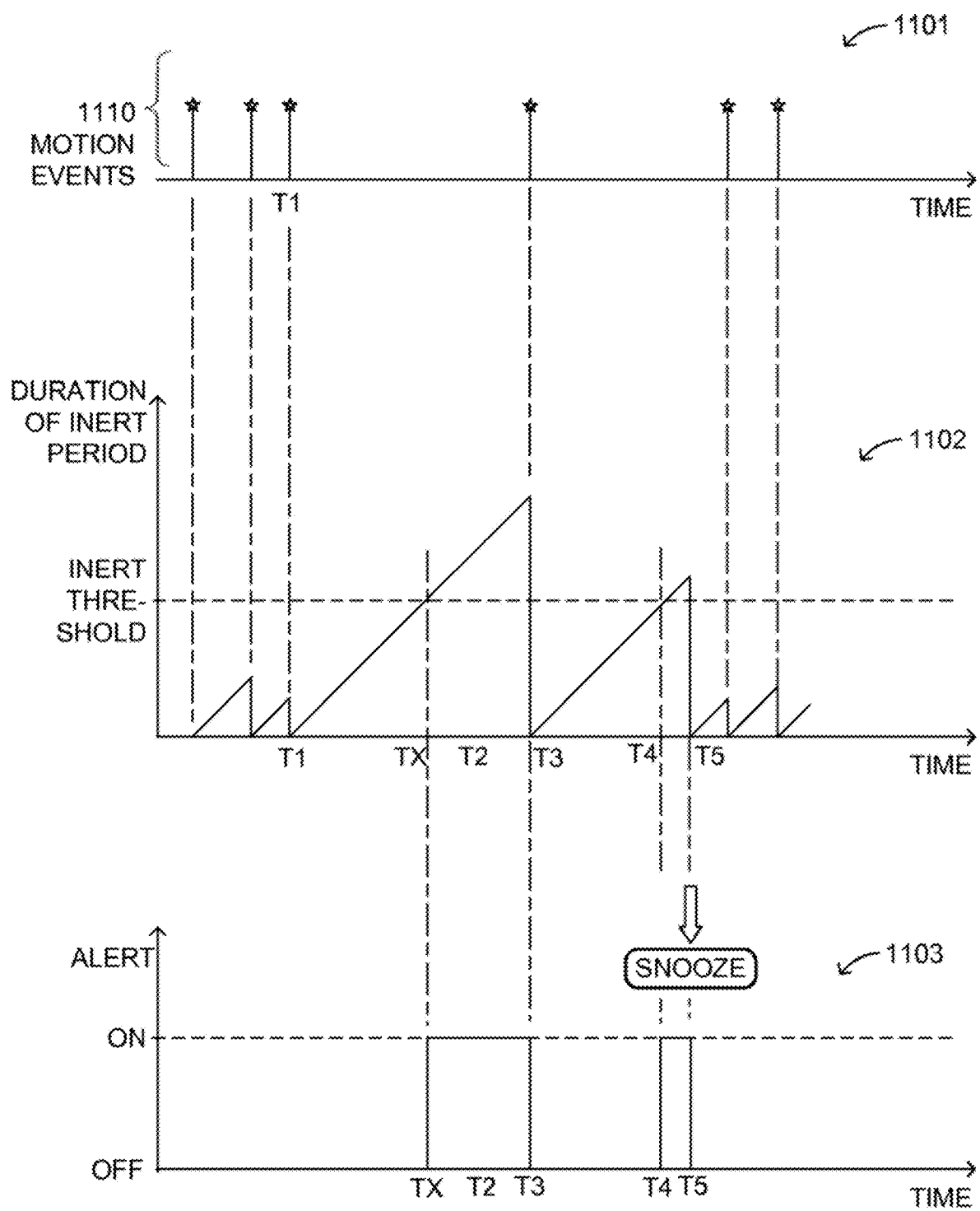
FIG. 11 shows sample timing diagrams for describing an alerting feature according to embodiments.

FIG. 11 shows sample timing diagrams 1101, 1102, 1103 according to embodiments. Diagram 1101 depicts motion events 1110 as stars plotted along a time axis. Each star may have variables additional to their moment of occurrence, or to the moment of starting. In the example of FIG. 11, only instantaneous motion events 1110 are shown, although that does not need to be the case. For example, they are not instantaneous if the patient is rising from a chair, or walking.

Motion event data may be extracted from motion events 1110. The motion event data may recognize and classify aspects of patient motion. For one example, aspects may be classified as patient-generated or not, depending on a magnitude of force, or acceleration. For another example, aspects may be classified as to whether they match typical motion patterns of means of transportation, such as periodicity and other statistics about frequency of motion, etc. For one more example, such aspects may be classified depending on the time of day, and according to previous patterns of the patient.

A motion statistic of the motion event data can thus be extracted for selected times along the time axis, for determining an amount of patient motion characterized as generated by the patient. The motion statistic may be intended for the amount of patient-generated motion.

Moreover, and as per the above, an inert period can be a duration during which the motion statistic is less than a motion threshold. It should be noted that inert periods for these purposes could be periods of patient motion which, however, are not characterized as being patient-generated. Examples of inert periods are now described.

Diagram 1102 can be used for depicting such inert periods. Its horizontal axis is a time axis parallel and coincident to the time axis of diagram 1101. Its vertical axis is also a time axis, which is of the same scale as the horizontal axis. The inert periods occur between the times of motion events 1110. In diagram 1102 ramps are also shown, as the durations of the inert periods could be measured by the aforementioned timer along the vertical axis. Accordingly, these durations can be shown on the vertical axis. The ramps are inclined at 45°, because the vertical axis is of the same scale as the horizontal axis.

In embodiments, it can be determined whether or not the duration of the inert period exceeds an inert threshold. In diagram 1102, this occurs for an inert period starting at a time T1 and ending at time T3; the threshold is crossed at time TX.

Diagram 1103 can be used for depicting actions of the output device. Its horizontal axis is a time axis parallel and coincident to the time axis of diagrams 1101 and 1102. In the example of diagram 1103, the alert is output between TX and T3, i.e. for the entire time during which the duration exceeds the inert threshold. This is not necessary, however, and a different alerting pattern may be initiated in response to the inert threshold being exceeded at time TX.

In such embodiments, the output device may be implemented in a number of ways, locally and/or remotely. In local embodiments, the WCD system may include the output device itself, for example as part of user interface 370. Given that the attention of the patient may be elsewhere, the human-perceptible alert can be an audible alert. In some embodiments, the output device is a component of a communication device, such as communication device 110. In some of those embodiments, the communication device is a standalone device, and in other embodiments the WCD system includes the communication device.

In remote embodiments, the output device can be collocated with the recipient, and alert the recipient. Examples of recipients are shown in FIG. 1: Health Care entity 191 and friends and family 192. In such embodiments, the WCD system may further include a communications module, which is configured to communicate to a recipient alert event data about the duration of the inert period exceeding the inert threshold. Communicating may be as described above, either through a backup comlink, or through a local comlink that continues by a remote comlink through a network, to computer 120, and from there to the recipient, etc. The alert event data may include information that generated the alert, such as one or more of the motion statistic, the duration of the inert period, and the event that the duration of the inert period exceeds the inert threshold.

In embodiments, a value for the inert threshold is downloaded from a communication network. This value may have been set by Health Care entity 191.

In embodiments, an inert threshold adjust input is received by the WCD system. In such embodiments, the inert threshold may become adjusted to a new value responsive to the received inert threshold adjust input. In some of these instances, the inert threshold adjust input is received via a communication device for example as seen in FIG. 7. In other instances, the WCD system further includes a user interface, such as UI 370, which is configured to receive the inert threshold adjust input; the inert threshold adjust input is then received via the user interface. In some embodiments, the new value is communicated to a recipient through a network, for example via a communications module configured to communicate this new value through the network.

In embodiments, a snooze feature is implemented for the alert about non-use. Returning to FIG. 11, the duration of the inert period can be determined as starting from a first moment. More particularly at diagram 1102, in the previously described inert period, the first moment was T1 and the inert period ended at T3 when there was another isolated motion event 1110—perhaps the user tapped the WCD system. At the time T3, the duration of the inert period was reset to zero, and resumed increasing from zero. At a subsequent time T4, the threshold is crossed again, and the alert is restarted as seen in diagram 1103.

At time TS, a snooze input is received, and the first moment becomes reset to a new value responsive to the received snooze input. In the example of FIG. 11, the new value is zero, although other values are possible. Resetting happened without a motion event from diagram 1101. The alert of diagram 1103 is thus turned off due to the received snooze input, at least temporarily.

There are a number of ways that the snooze input may be received. In some embodiments, the snooze input is received via a communication device such as communication device 110. In some embodiments, the WCD system further includes a user interface, such as UI 370, which is configured to receive the snooze input, and the snooze input is received via the user interface. The snooze input can be received as a result of a user actuating a Snooze button in the appropriate interface.

Even though the alert is turned off, this may be only temporary. In effect, a new inert period can be started and, when the threshold is crossed again, the alert can restart. It should be noted that, in the example of FIG. FIG. 7, the duration of the inert threshold (2 min) is the same regardless of whether the inert period was started from the end of the last motion event or actuating the snooze button. This need not be the case, however, and different inert thresholds may be implemented.

In some embodiments, the snooze feature can be disabled. For example, a Snooze-OFF input may be received, and the output device then does not output the human-perceptible alert responsive to the received Snooze-OFF input, even if the duration of the inert period exceeds the inert threshold. There are a number of ways that the Snooze-OFF input may be received.

In some embodiments, the Snooze-OFF input is received via a communication device such as communication device 110. In some embodiments, the Snooze-OFF input is received via a network, for example being set this way by Health Care entity 191. In some embodiments, the WCD system further includes a user interface, such as UI 370, which is configured to receive the Snooze-OFF input, and the Snooze-OFF input is received via the user interface. The Snooze-OFF input can be received as a result of a user actuating a Snooze-OFF button in the appropriate interface, for example as seen in FIG. 7.

FIG. 12 shows a flowchart 1200 for describing methods according to embodiments for a wearable cardiac defibrillator (WCD) system to work with an output device, whether the latter is part of the WCD system or not. The methods of flowchart 1200 may also be practiced by embodiments described elsewhere in this document.

According to an operation 1210, a patient may be defibrillated while wearing a support structure of the WCD system.

According to another, optional operation 1220, a value may be downloaded for an inert threshold. The value may be downloaded from a communication network.

According to another operation 1230, motion event data may be generated, for example by a motion sensor of the WCD system.

According to another operation 1240, the duration of an inert period may be determined. As with previously, the inert period can be a time interval during which the previously mentioned motion statistic of the motion event data is less than the previously mentioned motion threshold. Its duration may be determined in a number of ways, for example by counting time from its first moment until the present.

Embodiments may proceed in terms of an inert threshold. A value for it may be stored in a system memory. In embodiments, an inert threshold adjust input may be received, and the inert threshold may be adjusted to a new value in responsive thereto. The inert threshold adjust input may be received in a number of ways, such as via a communication device, a user interface of the WCD system, etc. In some embodiments, the inert threshold adjust input may be received locally, for example as shown in FIG. 7; in such cases, the new value can be communicated to a recipient through a network, for example via a communications module of the WCD system.

According to another operation 1250, it is determined whether or not the duration of the inert period exceeds this inert threshold. The inert threshold may be a value downloaded during operation 1220, or a pre-stored value, etc. If not, then execution may return to operation 1240 so as to determine the updated duration, and so on.

If at operation 1250 the answer is yes, then according to another operation 1260, the output device may be caused to output a human-perceptible alert. In some embodiments, the output device is located near the WCD system, and can even be part of it. In some embodiments, the output device is located remotely, in which case alert event data may be communicated to a recipient through a network, for example via a communications module of the WCD system. The alert event data may be about the duration of the inert period exceeding the inert threshold. In such cases the output device may alerts the recipient, in an auditory way, or visually by presenting alerts, records, etc.

According to another, optional operation 1270, it is inquired whether a snooze input has been received. The snooze input may be received in a number of ways, such as via a communication device, a user interface of the WCD system, etc. If at operation 1270 a snooze input has not been received, then execution may return to operation 1260. If at operation 1270 a snooze input has been received, then according to another, optional operation 1280, the first moment of the duration of the inert period may be reset to a new value, and execution may return to operation 1240.

This flowchart applies to where the inert threshold is always the same for when it is considered due to non-use and from the Snooze button, but would be correspondingly different if different thresholds were used.

In some embodiments, the snooze feature may be disabled. For example, a Snooze-OFF input may be received. In response, the output device might not be caused to output the human-perceptible alert responsive to the received Snooze-OFF input, even if the duration of the inert period exceeds the inert threshold. The Snooze-OFF input may be received in a number of ways, such as through a network, via a communication device, a user interface of the WCD system, etc.

In the methods described above, each operation can be performed as an affirmative step of doing, or causing to happen, what is written that can take place. Such doing or causing to happen can be by the whole system or device, or just one or more components of it. In addition, the order of operations is not constrained to what is shown, and different orders may be possible according to different embodiments. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily the present invention. Plus, any reference to any prior art in this description is not, and should not be taken as, an acknowledgement or any form of suggestion that this prior art forms parts of the common general knowledge in any country.

This description includes one or more examples, but that does not limit how the invention may be practiced. Indeed, examples or embodiments of the invention may be practiced according to what is described, or yet differently, and also in conjunction with other present or future technologies. Other embodiments include combinations and sub-combinations of features described herein, including for example, embodiments that are equivalent to: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in any number of ways, as will be apparent to a person skilled in the art after reviewing the present disclosure, beyond any examples shown in this document.

The following claims define certain combinations and subcombinations of elements, features and steps or operations, which are regarded as novel and non-obvious. Additional claims for other such combinations and subcombinations may be presented in this or a related document.

The embodiments of the invention in which an exclusive property or privilege is claimed are defined as follows:

1. A wearable cardiac defibrillator (WCD) system, comprising:
   a support structure configured to be worn by a patient;
   an external defibrillator configured to be coupled to the support structure and to defibrillate the patient while the support structure is worn by the patient;
   a motion sensor coupled to the support structure and configured to generate motion event data;
   a timer configured to determine a duration of an inert period during which a motion statistic of the motion event data is less than a motion threshold; and
   an output device configured to output a human-perceptible alert in response to the duration of the inert period exceeding an inert threshold.

2. The system of claim 1, in which
   the human-perceptible alert is an audible alert.

3. The system of claim 1, in which
   the output device is a component of a communication device.

4. The system of claim 1, further comprising:
   a communication module configured to communicate through a network to a recipient alert event data about the duration of the inert period exceeding the inert threshold, and
   the output device alerts the recipient.

5. The system of claim 4, in which
   the alert event data includes at least one of the motion statistic, the duration of the inert period, or the event that the duration of the inert period exceeds the inert threshold.

6. The system of claim 1, in which
   a value for the inert threshold is downloaded from a communication network.

7. The system of claim 1, in which
   an inert threshold adjust input is received, and
   the inert threshold becomes adjusted to a new value responsive to the received inert threshold adjust input.

8. The system of claim 7, further comprising:
   a user interface configured to receive the inert threshold adjust input, and
   the inert threshold adjust input is received via the user interface.

9. The system of claim 7, further comprising:
   a communications module configured to communicate the new value to a recipient through a network.

10. The system of claim 1, in which
    the duration of the inert period is determined as starting from a first moment,
    a snooze input is received, and
    the first moment becomes reset to a new value responsive to the received snooze input.

11. The system of claim 10, further comprising:
    a user interface configured to receive the snooze input, and
    the snooze input is received via the user interface.

12. The system of claim 1, in which
a Snooze-OFF input is received, and
the output device does not output the human-perceptible alert responsive to the received Snooze-OFF input even in response to the duration of the inert period exceeding the inert threshold.

13. A method for a wearable cardiac defibrillator (WCD) system to work with an output device, the WCD system including a support structure configured to be worn by a patient, an external defibrillator configured to be coupled to the support structure and configured to defibrillate the patient while the support structure is worn by the patient, a motion sensor coupled to the support structure, and a timer, the method comprising:
defibrillating the patient while the support structure is worn by the patient;
generating, by the motion sensor, motion event data;
determining a duration of an inert period during which a motion statistic of the motion event data is less than a motion threshold;
determining whether the duration of the inert period exceeds an inert threshold; and
in response to a determination that the duration of the inert period exceeded the inert threshold, causing the output device to output a human-perceptible alert.

14. The method of claim 13, in which
the human-perceptible alert is an audible alert.

15. The method of claim 13, in which
the WCD system further includes a communications module, and further comprising:
communicating, via the communications module through a network, to a recipient alert event data about the duration of the inert period exceeding the inert threshold, and
in which the output device alerts the recipient.

16. The method of claim 15, in which
the alert event data includes at least one of the motion statistic, the duration of the inert period, or the event that the duration of the inert period exceeds the inert threshold.

17. The method of claim 13, further comprising:
receiving an inert threshold adjust input; and
adjusting the inert threshold to a new value responsive to the received inert threshold adjust input.

18. The method of claim 13, in which
the duration of the inert period is determined as starting from a first moment, and
further comprising:
receiving a snooze input; and
resetting the first moment to a new value responsive to the received snooze input.

19. The method of claim 13, further comprising:
receiving a Snooze-OFF input, and
in which the output device is not caused to output the human-perceptible alert responsive to the received Snooze-OFF input even in response to the duration of the inert period exceeding the inert threshold.

20. A wearable cardiac defibrillator (WCD) system comprising:
a non-transitory computer-readable storage medium storing one or more programs which, when processed by at least one processor of the WCD system, the WCD system including a support structure configured to be worn by a patient, an external defibrillator coupled to the support structure, a motion sensor coupled to the support structure, and a timer coupled to the support structure, the WCD system performs operations comprising:
defibrillating the patient while the support structure is worn by the patient;
generating, by the motion sensor, motion event data;
determining a duration of an inert period during which a motion statistic of the motion event data is less than a motion threshold;
determining whether the duration of the inert period exceeds an inert threshold; and
in response to a determination that the duration of the inert period exceeded the inert threshold, causing the output device to output a human-perceptible alert.

* * * * *